United States Patent
Duan et al.

(10) Patent No.: US 10,212,340 B2
(45) Date of Patent: Feb. 19, 2019

(54) MEDICAL IMAGING SYSTEM AND METHOD FOR OBTAINING MEDICAL IMAGE

(71) Applicants: Ran Duan, Beijing (CN); Di Li, Beijing (CN)

(72) Inventors: Ran Duan, Beijing (CN); Di Li, Beijing (CN)

( * ) Notice: Subject to any disclaimer, the term of this patent is extended or adjusted under 35 U.S.C. 154(b) by 216 days.

(21) Appl. No.: 14/939,444

(22) Filed: Nov. 12, 2015

(65) Prior Publication Data
US 2016/0057343 A1 Feb. 25, 2016

Related U.S. Application Data

(63) Continuation-in-part of application No. PCT/CN2014/077306, filed on May 12, 2014.

(30) Foreign Application Priority Data

| May 13, 2013 | (CN) | 2013 1 0174062 |
| May 13, 2013 | (CN) | 2013 1 0174164 |
| Apr. 21, 2014 | (CN) | 2014 1 0160850 |

(51) Int. Cl.
*H04N 5/232* (2006.01)
*A61B 5/00* (2006.01)
(Continued)

(52) U.S. Cl.
CPC ....... *H04N 5/23235* (2013.01); *A61B 5/0077* (2013.01); *A61B 5/0088* (2013.01);
(Continued)

(58) Field of Classification Search
CPC ............ H04N 5/23235; H04N 5/2226; H04N 5/2253; H04N 5/77; H04N 5/91; A61B 5/0077; A61B 5/0088; G06T 3/4076
See application file for complete search history.

(56) References Cited

U.S. PATENT DOCUMENTS

| 6,414,708 B1 * | 7/2002 | Carmeli ............. A61B 1/00045 348/42 |
| 2005/0156816 A1 * | 7/2005 | Repetto ................ G02B 27/017 345/7 |

(Continued)

FOREIGN PATENT DOCUMENTS

| CN | 1373969 A | 10/2002 |
| CN | 101610354 A | 12/2009 |
| CN | 102014240 A | 4/2011 |

OTHER PUBLICATIONS

CN 101610354 A_English Abstract.
CN 102014240 A_English Abstract.
CN1373969 A_English Abstract.

*Primary Examiner* — Christopher G Findley
(74) *Attorney, Agent, or Firm* — Ladas & Parry LLP

(57) ABSTRACT

A medical imaging system is disclosed in the present invention, including a medical image acquisition device and medical image processing system. Said medical image acquisition device includes: an acquisition apparatus for acquiring image signals in a medical process from a first viewing angle of a doctor; and a signal processing apparatus for performing a first processing on the acquired image signals and then sending digital image signals in the form of data stream. Said medical image processing system includes: a signal transmission module for receiving a data stream of digital image signals from a medical image acquisition device; and an image processing module for processing the received data stream of digital image signals in real time according to a predetermined image processing method so as to obtain optimized digital medical image signals.

10 Claims, 4 Drawing Sheets

(51) Int. Cl.
G06T 3/40 (2006.01)
H04N 5/225 (2006.01)
H04N 5/77 (2006.01)
H04N 5/91 (2006.01)
H04N 5/222 (2006.01)
H04N 7/18 (2006.01)

(52) U.S. Cl.
CPC ......... G06T 3/4076 (2013.01); H04N 5/2226 (2013.01); H04N 5/2253 (2013.01); H04N 5/77 (2013.01); H04N 5/91 (2013.01); H04N 7/185 (2013.01)

(56) References Cited

U.S. PATENT DOCUMENTS

| | | | |
|---|---|---|---|
| 2010/0074552 A1* | 3/2010 | Sun | G06T 5/003 382/264 |
| 2012/0130257 A1* | 5/2012 | Heanue | A61B 5/0059 600/476 |

* cited by examiner

MEDICAL IMAGING SYSTEM AND METHOD FOR OBTAINING MEDICAL IMAGE

CROSS REFERENCE APPLICATION

This application is a continuation-in-part of International Application PCT/CN2014/077306 filed 12 May 2014 which claims the benefit of Chinese Applications Numbers 201310174164.1 filed 13 May 2013, 201310174062.X filed 13 May 2013 and 201410160850.8 filed 21 Apr. 2014, the content of which are incorporated herein by reference.

TECHNICAL FIELD

The present invention relates to the field of medical imaging technology. More particularly, the present invention relates to a medical image acquisition device, a medical image processing system, and a medical imaging system, and to a method for obtaining medical images.

BACKGROUND

During a doctor's treatment on lesions, especially during a surgeon's operation or a dentist's dental treatment, there is a need to record the images of the operation and treatment process, so as to record the operation process or to be used for education or research.

The traditional recording of medical images is performed by a single photographer with a hand-held camera device, just like a photographer shoots a documentary. However, there are many defects in this manner, for example, the single photographer has to be involved in the operation, and both the huge camera device and the photographer need to be sterilized. Moreover, the photographer has to shoot from a very close distance during the operation, and this may influence the doctor. Serious consequence will be caused if the hand-held device drops in the sterile area. On the other hand, since the shooting angle of the photographer is different from the viewing angle of the doctor, the recorded image may not be shot from the most ideal angle.

Currently, a head-wearing device for shooting medical images is proposed. This device is worn on the doctor's head and has one or two micro cameras so as to record the operation throughout. However, this device can also be used as power supply and memory, and hence has a heavy weight and a large volume. This goes against the doctor's free movement and the device's firm wear. In addition, since the micro camera itself has a limited resolution, the recorded images have a poor definition.

SUMMARY

In view of the above-mentioned problems, according to an aspect of the present invention, a medical image acquisition device which can well photograph images in medical process is provided.

In an embodiment of the present invention, a medical image acquisition device includes:

an acquisition apparatus for acquiring image signals from a first viewing angle of a surgeon; and a signal processing apparatus for performing a first processing on the acquired image signals and then sending digital image signals in the form of data stream.

In an alternative embodiment, said acquisition apparatus is a digital photographic apparatus, and the acquired image signals are digital image signals. Said signal processing apparatus performs said first processing on the acquired image signals and then sends said digital image signals in the form of data stream, in which said signal processing caches said digital image signals and then sends the data stream of said digital image signals by a wireless transmission module. In general the digital photographic apparatus directly reads digital signals from a camera.

In an alternative embodiment, said acquisition apparatus is an analog photographic apparatus, and the acquired image signals are analog image signals. Said signal processing apparatus includes: an analog-digital conversion module for converting said analog image signals into digital image signals; and a first processing module for caching said digital image signals and then sending the data stream of said digital image signals by a wireless transmission module.

In an alternative embodiment, said medical image acquisition device is a wearable acquisition device, wherein said acquisition apparatus is a head-wearing acquisition apparatus, an ear-wearing acquisition apparatus or a spectacles-type acquisition apparatus.

According to another aspect of the present invention, a medical image processing system is provided, including:

a signal transmission module for receiving a data stream of digital image signals from a medical image acquisition device; and an image processing module for processing the received data stream of digital image signals in real time according to a predetermined image processing method so as to obtain optimized digital medical image signals.

In an alternative embodiment, said medical image processing system further includes a storage module for storing the optimized digital medical image signals; or said image processing module is also used to send the optimized digital medical image signals to a remote storage center through a signal transmission module.

In an alternative embodiment, the medical image processing system further includes: an image output interface for providing, according to display instructions from said image processing module, the optimized digital medical image signals to a display apparatus for displaying images.

In an alternative embodiment, the predetermined image processing method is an improved Gauss-Seidel iterative or Richardson-Lucy iterative algorithm.

In an alternative embodiment, said image processing module is a FPGA chip or a CPLD chip.

In an alternative embodiment, the medical image processing system further includes: an information entry module for receiving patient information input through the display apparatus or imported from a database. In an alternative embodiment, the medical image processing system further includes said image processing module which is also used to perform corresponding processing, according to the received image processing control instructions, on the optimized digital medical image signals, wherein said image processing control instructions are received through control interfaces on the display apparatus and sent to the medical image processing system, or received through a voice control module.

According to yet another aspect of the present invention, a system is provided, including the medical image acquisition device and the medical image processing system, wherein said medical image acquisition device includes: an acquisition apparatus for acquiring image signals in a medical process from a first viewing angle of a doctor; and a signal processing apparatus for performing a first processing on the acquired image signals and then sending digital image signals in the form of data stream; and said medical image processing system is provided, including: a signal transmission module for receiving a data stream of digital image signals from a medical image acquisition device; an image processing module for processing the received data stream of digital image signals in real time according to a predetermined image processing method so as to obtain optimized digital medical image signals.

According to yet another aspect of the present invention, a method for obtaining medical images is provided, including:

a medical image acquisition device acquiring image signals in a medical process from a first viewing angle of a surgeon;

said medical image acquisition device performing a first processing on the acquired image signals and then sending out digital image signals in the form of data stream;

a medical image processing system receiving a data stream of digital image signals sent by said medical image acquisition device; and said medical image processing system processing the received data stream of digital image signals in real time according to a predetermined image processing method so as to obtain optimized digital medical image signals.

In an alternative embodiment, the method further includes: said medical image processing system storing the optimized digital image signals locally or sending them to a remote storage center.

In an alternative embodiment, the predetermined image processing method is an improved Gauss-Seidel iterative or Richardson-Lucy iterative algorithm.

In an alternative embodiment, said medical image processing system provides the optimized digital medical image signals to a display apparatus for displaying images.

In an alternative embodiment, the method further includes: said medical image processing system receiving patient information input through the display apparatus or imported from a database; or said medical image processing system performing corresponding processing, according to the received image processing control instructions, on the optimized digital medical image signals, wherein said image processing control instructions are received through control interfaces on the display apparatus and sent to the medical image processing system, or received through a voice control module.

According to yet another aspect of the present invention, a volatile computer readable storage medium is provided, comprising a program, when executed, implementing following operations:

receiving a data stream of digital image signals sent by a medical image acquisition device;

processing the received data stream of digital image signals in accordance with a predetermined image processing method in real time so as to obtain optimized digital medical image signals.

In an alternative embodiment, the program, when executed, implements following operation: said medical image processing system storing the optimized digital image signals locally, sending them to a remote storage center, to the "cloud", specific data server or stores in any other manner.

In an alternative embodiment, the predetermined image processing method is an improved Gauss-Seidel iterative or Richardson-Lucy iterative algorithm.

In an alternative embodiment, the program, when executed, implements following operation: providing the optimized digital medical image signals to a display apparatus for displaying images.

In an alternative embodiment, the program, when executed, implements following operations: receiving patient information inputting through the display apparatus or imported from a database; or performing corresponding processing, according to the received image processing control instructions, on the optimized digital medical image signals, wherein said image processing control instructions are received through control interfaces on the display apparatus and sent to the medical image processing system, or received through a voice control module.

With the medical image acquisition device according to the embodiments of the present invention, the acquired image signals can truly reproduce the operation process since the image signals in the operation process are acquired from the first viewing angle of the surgery. The medical image processing system according to the embodiments of the present invention can optimize the data stream of digital image signals so that clearer surgery images can be obtained. The medical imaging system and the method for obtaining medical images according to the embodiments of the present invention can well provide images of the operation process or diagnosis and treatment process involving a certain doctor so as to facilitate searching, teaching, and management.

BRIEF DESCRIPTION OF THE DRAWING

The foregoing and/or other aspects and advantages of the present invention will be apparent and easy to understand from the following description of embodiments taken in conjunction with the accompanying drawings in which.

DETAILED DESCRIPTION

Figure 1:
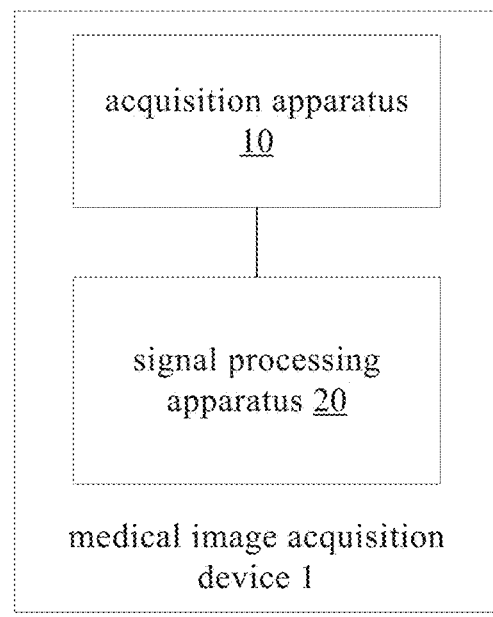
FIG. 1 illustrates a structure schematic of a medical image acquisition device according to an embodiment of the present invention.

Embodiments of the present invention are described in detail below, examples of which are illustrated in the accompanying drawings. The same or like reference numerals denote the same or like elements or elements having the same or like functions throughout. The embodiments described with reference to the accompanying drawings below are exemplary, and only used to explain the present invention rather than construed as limitation to the present invention. Several different examples or instances are provided in disclosure hereinafter to embody different structures of the present invention. In order to simplify the disclosure, components and configurations in certain instances are described hereinafter. Of course, they are illustrative only not for purpose of limitation. In addition, reference numerals or alphabets could be repeated in different instances in the present invention. This repetition is for a purpose of simplification and clarity, and not intended to indicate relationships between various embodiments and/or configurations set forth herein.

FIG. 1 illustrates a structure schematic of a medical image acquisition device according to an embodiment of the present invention. As shown in FIG. 1, the acquisition device 1 includes: an acquisition apparatus 10 for acquiring image signals in a medical process from a first viewing angle of a surgeon; and a signal processing apparatus 20 for performing a first processing on the acquired image signals and then sending out digital image signals in the form of data stream.

In the embodiment of the present invention, the "first viewing angle" means viewing an operation from the surgeon's own viewing angle. In this way, the image signal acquired by the acquisition device is equivalent to that viewed behind the surgeon, so that the image viewed through a display is that viewed by the surgeon.

As to the signal processing apparatus, video streams are cached in a video encoder in the signal processing apparatus, and then written into a video file. At the same time, the video streams are uploaded and sent in a form of, such as, rstp, or in common forms of sending video streams. The A/D conversion module uses general A/D conversion means or any equivalent means to achieve A/D conversion.

In the embodiment of the present invention, the acquisition device used for acquiring a medical image may be a wearable acquisition device. In an embodiment of the present invention, the wearable acquisition device may be of integrated type, that is, the acquisition apparatus and signal processing apparatus are disposed in one device. In this way, the surgeon just needs to put the medical image acquisition device on his/her head. In another embodiment of the present invention, the wearable acquisition device may be of split type, that is, the acquisition apparatus and signal processing apparatus are two separate devices. The signal processing apparatus may be located in a certain part of the surgeon's body, such as waist, while the acquisition apparatus may be located on a certain part of the surgeon's head, like a head-wearing acquisition apparatus, an ear-wearing acquisition apparatus or a spectacles-type acquisition apparatus. For instance, the spectacles-type acquisition apparatus may be like glasses or spectacles with a camera located above a user's eyes. The camera may be embedded in the glasses or spectacle frames. For the head-wearing acquisition apparatus, its camera is located on the user's forehead. The head-wearing acquisition apparatus may be worn on a head like a head lamp. The ear-wearing acquisition apparatus may be directly worn on the ear, around the ear and the like. For the ear-wearing acquisition apparatus, its camera is secured by the user's ear, so the camera is located on the user's side face. Therefore, the camera is kept to be parallel to the first viewing angle of the surgeon, so that the acquired image is that of the operation content viewed from the first viewing angle of the surgeon.

In an embodiment of the present invention, the acquisition apparatus 10 may be a digital photographic apparatus. In this way, the acquired image signals are digital image signals. Then, the signal processing apparatus 20 performs the first processing on the acquired image signals and then sends out the processed digital image signals in the form of data stream. Preferably, the signal processing apparatus 20 may store the digital image signals acquired by the acquisition apparatus into a local cache, and then send the digital image signals in the form of data stream using a sending module.

In another embodiment of the present invention, the acquisition apparatus 10 might be an analog photographic apparatus. In this embodiment, the signal processing apparatus 20 includes: an A/D (Analog/Digital) conversion module for converting the acquired analog image signals into digital image signals; and a first processing module for caching the digital image signals and then sending them in the form of data stream.

Figure 2:
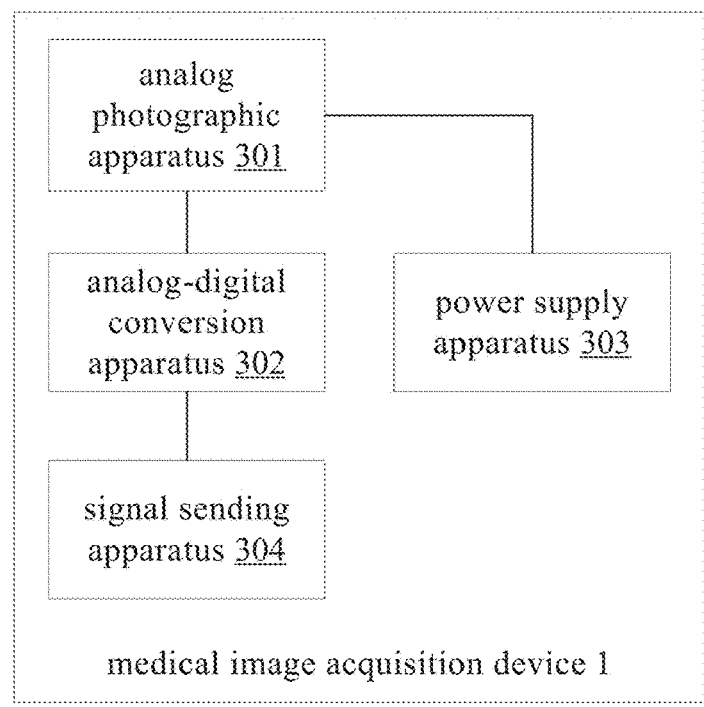
FIG. 2 illustrates a structure schematic of a medical image acquisition device according to an embodiment of the present invention, wherein the acquisition apparatus is an analog photographic apparatus.

FIG. 2 illustrates a structure schematic of a medical image acquisition device according to an embodiment of the present invention, wherein the acquisition apparatus is an analog photographic apparatus. As shown in FIG. 2, the analog photographic apparatus 301 of the medical image acquisition device is a micro analog photographic apparatus, which is used for shooting the operation in the medical process. Said medical image acquisition device also includes: an A/D conversion module 302 for converting the shot analog image signals into digital image signals; a power supply apparatus 303 for supplying the micro analog photographic apparatus with electricity; and a signal sending apparatus 304 for sending the digital image signals from the A/D conversion module to the medical image processing system.

Preferably, the A/D conversion apparatus 302, the power supply apparatus 303, and the signal sending apparatus 304 may be individual modules disposed in the signal processing apparatus 20. In this connection, the signal processing apparatus caches the digital image signals converted from the A/D conversion module, and then sends them out in the form of data stream using the signal sending apparatus.

In an embodiment of the present invention, the photographic apparatus may include one or more micro cameras, preferably, high definition (HD) cameras. The sending module or signal sending apparatus may send signals using a wireless transmission mode, such as Bluetooth, Wi-Fi and any means equivalent to Bluetooth and Wi-Fi, so as not to interfere with the surgeon's free movement during the operation.

Figure 3:
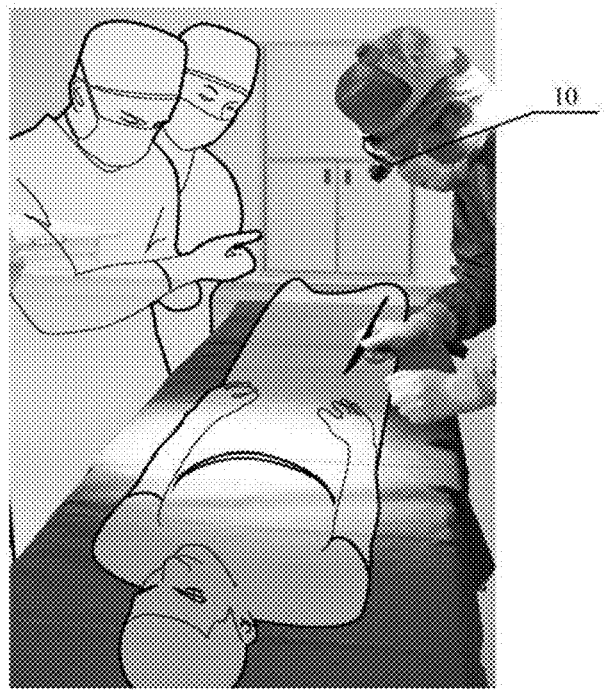
FIG. 3 schematically illustrates an example of a head-wearing acquisition device according to an embodiment of the present invention.

FIG. 3 schematically illustrates an example of the head-wearing acquisition device according to an embodiment of the present invention. As shown in FIG. 3, the photographic apparatus of the head-wearing acquisition device is located on the surgeon's forehead, so as to acquire the image signals from the first viewing angle of the surgeon in the medical process. It should be noted that the surgeon mentioned in the present invention includes, but not limits to, a doctor performing operation, also includes, such as, other doctors conducting assistances in the operation room. Preferably, the surgeon is the doctor performing operation.

Figure 4:
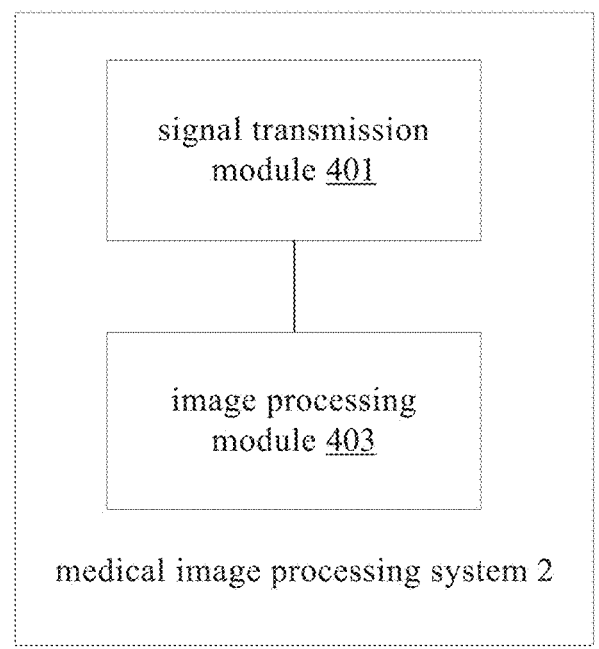
FIG. 4 illustrates a structure schematic of a medical image processing system according to an embodiment of the present invention.

FIG. 4 illustrates a structure schematic of a medical image processing system according to an embodiment of the present invention. As shown in FIG. 4, the medical image processing system 2 includes: a signal transmission module 401 for receiving the data stream of digital image signals from the medical image acquisition apparatus; and an image processing module 403 for processing the received data stream of digital image signals in real time in accordance with a predetermined image processing method so as to obtain optimized digital medical image signals.

With the medical image processing system of the present invention, the received data stream of digital image signals may be processed in real time and then stored. In a preferred embodiment of the present invention, said predetermined image processing method may be an improved Gauss-Seidel iterative or Richardson-Lucy iterative algorithm. In this connection, the shot surgery images can be optimized, so as to obtain clearer ones and remedy deficiency in definition of the micro photographic apparatus itself.

In the description of this specification, the terms below have specific meanings. In particular, "matrix data" means data obtained through processing images obtained by viewing an object through an instrument. An "instrument characteristic matrix" represents a matrix containing responsive degrees of the instrument in respective directions, and can be obtained by experiments. A "re-convolution matrix" is a matrix obtained through re-convolving the matrix data with the transposed matrix of the instrument characteristic matrix. Finally, a "normalized re-convolution matrix" is a matrix calculated with related algorithms, and indicates that a matrix A has saltations and large values in the case of a matrix B.

In an embodiment of the present invention, the image processing module 403 processes the digital image signals in accordance with the predetermined image processing method, which includes steps as follows:

S1. selecting an instrument characteristic matrix $p(i,j)$;
S2. for each frame of matrix data $d(i)$ of an input image, convolving $d(i)$ with $p^T(i,j)$ as a re-convolution matrix $c(i)$;
S3. proceeding to step S9 when the matrix data $d(i)$ has no background or the background $b(i)$ is known;
S4. calculating a normalized re-convolution matrix $c^*(i)$ of $p(i,j)$ and $d(i)$;

$$c^*(i) = \frac{M\sum_k [p(k,i)d(k)] - \sum_k p(k,i)\sum_k d(k)}{M\sum_k [p(k,i)]^2 - [\sum_k p(k,i)]^2};$$

where M are matrix data elements of each line of $d(i)$;
S5. setting a threshold $f_m$, and determining whether each point of $c^*(i)$ is greater than $f_m$, if so, then determining whether this point is a data saltation point or has a value greater than that of the background, calculating $d_b(k)=d(k)-p(k,i_s)f_s$, and subtracting the value of this point;
where $f_s$ satisfies $\Sigma_i\{c_b(i')-[c^*(i')-f_s c_s(i',i_s)]\}^2 = \min$, and where $d_b(k)$ is a matrix data after subtracting the data saltation point and the data point having a value greater than that of the background, $c_b(i)$ is a re-convolution matrix of $d_b(k)$ and $p(i,j)$, and $c_s(i;i_s)$ is a re-convolution matrix of $p(i,j)$ and itself:

$$c_s(i;i_s) = \frac{M\sum_k [p(k,i)p(k,i_s)] - \sum_k p(k,i)\sum_k p(k,i_s)}{M\sum_k [p(k,i)]^2 - [\sum_k p(k,i)]^2}$$

repeating the above steps until all data points in $c^*(i)$ are less than $f_m$, so that matrix data, denoted as $d_b(k)$, in which the data saltation point and the data point having a value greater than that of the background are removed, is obtained;
S6. calculating the convolution of $d_b(k)$ and $p(i,j)$, denoted as $c_b(i)$;
S7. restoring the background of data using the Gauss-Seidel iterative and Richardson-Lucy iterative algorithms, in which a set upper limit is that all values are greater than or equal to 0;

S8. repeating step S7 until a convergence result is obtained as a reconstructed background data, denoted as $b^{(l)}(i)$, where the superscript 1 indicates iterating one time;
S9. under a limitation of $b^{(l)}(i)$ or the background known in advance, calculating real matrix data, denoted as $f^{(l)}(i)$, by the Gauss-Seidel iterative or Richardson-Lucy iterative algorithm, where the superscript 1 indicates iterating one time and $f^{(l)}(i)$ represents the result after a first iteration;
S10. letting $f^{(l)}(i)$ satisfy a normalization condition:

$$\sum_k \sum_i p(k,i) f^{(1)}(i) = \sum_k d(k)$$

where $f^{(l)}(i)$ satisfying the normalization condition is the restored matrix data.

At step S7, the background of data may be restored with the Gauss-Seidel iterative algorithm by following formula:

$$b^{(l)}(i) = \frac{1}{p_1(i,i)}\left[c_b(i) - \sum_{j\neq i} p_1(i,j) b^{(l-1)}(i)\right]$$

$$b^{(1)}(i) \geq 0$$

Where $f^{(l)}(i)$ represents the result after the first iteration, and $p_1(i,i)$ is a result of multiplying $p(i,j)$ with $p^T(i,j)$.

Alternatively, at step S7 the background of data may be restored with the Gauss-Seidel iterative algorithm having a convergence factor by following formula:

$$b^{(l)}(i) = \frac{\alpha}{p_1(i,i)}$$

$$\left[c_b(i) - \sum_{j=1}^{i-1} p_1(i,j) b^{(l)}(i) - \sum_{j=i+1}^{N} p_1(i,j) b^{(l-1)}(i) + (1-\alpha) b^{(l-1)}(i)\right]$$

$$b^{(l)}(i) \geq 0$$

where $\alpha$ is the convergence factor between 0 and 1.

In addition, as another alternative, at step S7, the background of data may also be restored with the Richardson-Lucy iterative algorithm by following formula:

$$b^{(l)}(i) = b^{(l-1)}(i) \frac{\Sigma_j \frac{p(j,i)d(j)}{\Sigma_{i'} p(j,i') b^{(l-1)}(i)}}{\Sigma_j p(j,i)}$$

$$b^{(1)}(i) \geq 0.$$

Correspondingly, at step S9, the real matrix data is calculated with the Gauss-Seidel iterative algorithm by following formula:

$$f^{(l)}(i) = \frac{1}{p_1(i,i)}\left[c(i) - \sum_{j\neq i} p_1(i,j) f^{(l-1)}(j)\right]$$

$$f^{(l)}(i) \geq b^{(l)}(i).$$

In addition, at step S9, the real matrix data may also be calculated with the Gauss-Seidel iterative algorithm having a convergence factor by following formula:

$$f^{(l)}(i) = \frac{\alpha}{p_1(i,i)} \left[ c(i) - \sum_{j=1}^{i-1} p_1(i,j)f^{(l)}(j) - \sum_{j=i+1}^{N} p_1(i,j)f^{(l-1)}(j) + (1-\alpha)f^{(l-1)}(i) \right]$$

$$f^{(l)}(i) \geq b^{(l)}(i).$$

As another alternative, at step S9, the real matrix data may also be calculated with the Richardson-Lucy iterative algorithm by following formula:

$$f^{(l)}(i) = f^{(l-1)}(i) \frac{\sum_j \frac{p(j,i)d(j)}{\sum_{i'} p(j,i')f^{(l-1)}(i')}}{\sum_j p(j,i)}$$

$$f^{(l)}(i) \geq b^{(l)}(i).$$

In the embodiments of the present invention, the Gauss-Seidel iterative or Richardson-Lucy iterative algorithm used at steps S7 and S9 are commonly used Gauss-Seidel iterative or Richardson-Lucy iterative algorithm. In the image processing methods of embodiments of the present invention, the background is firstly processed so that information of weak sources can be well retained. During the iterations, parameters of the imaging system can be used repeatedly so as to improve the restoration ability. The final optimizing condition is not a single parameter, but a matrix determinate condition, which causes less information loss. The image processed by the above-mentioned processing method maximizes the restoration of image information. By taking full advantage of prior knowledge of the instruments and objects, the image restoration and specific information extraction can be achieved within a larger dynamic range. With the medical image processing system of the present invention, clearer surgery images can be obtained so as to remedy deficiency in the definition of the micro photographic apparatus itself. In the embodiments of the present invention, the image processing module may be a FPGA chip or CPLD chip so as to meet the real-time requirement of image processing.

In addition, the image processing may be achieved on parallel operating carriers, such as common ARM or GPU and the like, using general image processing methods or any equivalent processing methods.

In an embodiment of the present invention, the medical image processing system may be further designed to provide specialized visual interfaces and a simple and convenient image video functionality. For an example, the received data stream of images is stored and archived in real time, so corresponding video screenshots can be extracted by time. In an embodiment of the present invention, in order to obtain clear and optimized digital medical image signals, the medical image processing system can also perform other processing on the data stream of digital medical image signals, wherein the other processing may include one or more of the following: image torsion correction, center positioning in a operation region under a camera lens, fuzzy correction in motion images photographing, surgery field automatic detection, jitter/shaking/fuzzy correction, color manipulation, white balance, medical special color processing, and so on. In addition, the medical image processing system may also include an information entry module for receiving patient information input through a display apparatus. The information entry module can provide an interface for filling patient information, such as name, date and comments and the like, which is then archived into a database. The information entry module can also receive the patient information imported from the database. In an embodiment of the present invention, the information entry module can also perform indexing on the stored images based on the received patient information, or print the extracted static images and so on.

Figure 5:
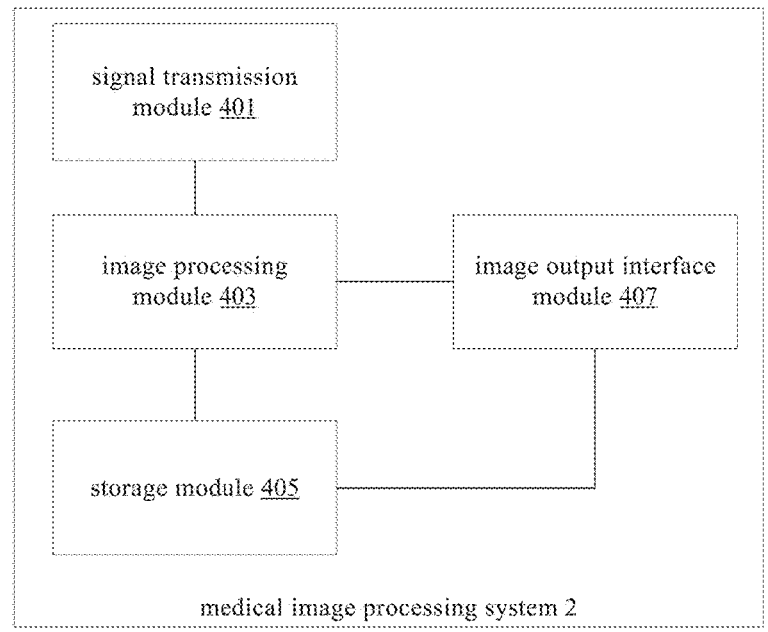
FIG. 5 illustrates a structure schematic of a medical image processing system according to another embodiment of the present invention.

FIG. 5 is a structure schematic of the medical image processing system according to another embodiment of the present invention. Besides the signal transmission module 401 and the image processing module 403, the medical image processing system 2 further includes a storage module 405 for storing said optimized digital medical image signals. In an alternative embodiment of the present invention, the image processing module 403 is also used to send the optimized digital medical image signals to a remote storage center, such as a specific data server or cloud storage center, by using the signal transmission module 401. In an alternative embodiment of the present invention, the medical image processing system 2 may also include an image output interface 407 for providing, according to control instructions from the image processing module, the optimized digital medical image signals to the display apparatus for displaying images. The display apparatus may be, for example, desktop computers, laptop computers, tablet computers, and any other display device. In an embodiment of the present invention, a user can, through control interfaces on the display apparatus, control the playing of the optimized digital image signals, or perform corresponding controls on the image processing of the image processing module. For instance, after the user inputs an instruction of image torsion correction through the control interface on the display apparatus, the display apparatus transfers the instruction of image torsion correction to the image processing module, which then performs the image torsion correction on the digital medical image signals according to the received instruction of image torsion correction. The image processing module can also perform corresponding image processing on the digital medical image signals according to the control instruction of image processing received through a voice control module. In addition, the medical image processing system may also share the optimized digital medical image signals with other devices in real time through the signal transmission module, for example, with other devices on a local area network or internet through wireless technologies such as Bluetooth, WiFi, and any means equivalent to Bluetooth and WiFi.

Figure 6:
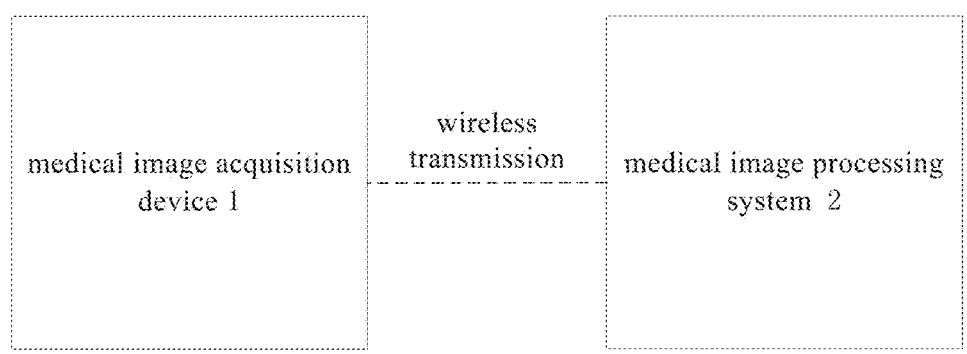
FIG. 6 illustrates a structure schematic of a medical imaging system according to an embodiment of the present invention.

FIG. 6 illustrates a structure schematic of the medical imaging system according to an embodiment of the present invention. As shown in FIG. 6, the medical imaging system includes the medical image acquisition device 1 according to various embodiments of the present invention, and the medical image processing system 2 according to various embodiments of the present invention, wherein the embodiments of the medical image acquisition and the medical image processing system may refer to descriptions thereof, respectively, and will not be described again.

Figure 7:
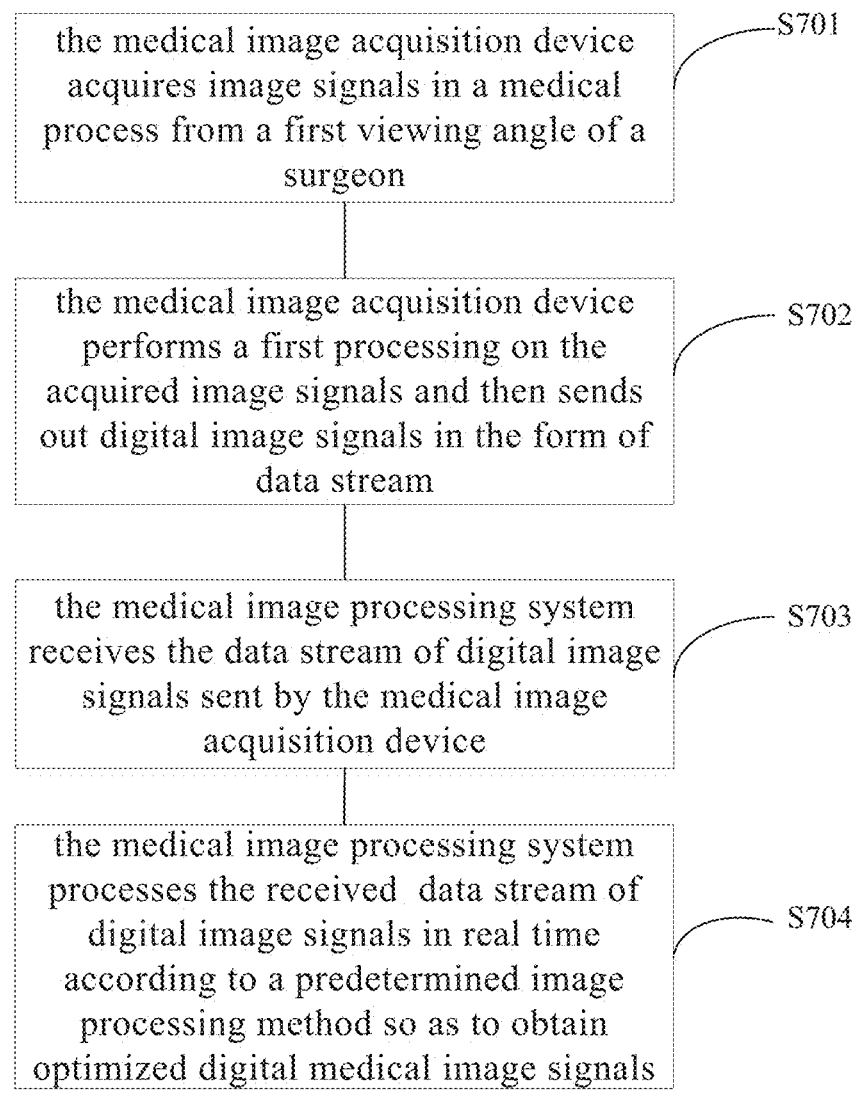
FIG. 7 illustrates a schematic flow chart of obtaining medical images according to an embodiment of the present invention.

Correspondingly, a method for obtaining the medical images is also provided in the present invention. FIG. 7 illustrates the method for obtaining the medical images according to an embodiment of the present invention. With reference to FIG. 7, this method for obtaining the medical images includes steps as follows.

At step S701, the medical image acquisition device acquires image signals in a medical process from a first viewing angle of a surgeon.

At step S702, the medical image acquisition device performs a first processing on the acquired image signals, and then sends out digital image signals in the form of data stream.

Preferably, after performing the first processing on the acquired image signals, the medical image acquisition device sends a data stream of the processed image signals via wireless transmission. If the image signals acquired by the medical image acquisition device are analog, then the first processing includes converting the analog image signals to digital image signals, caching the digital image signals and sending them in the form of data stream. If the image signals acquired by the medical acquisition device are digital, then the first processing includes caching the digital image signals and sending them in the form of data stream.

At step S703, the medical image processing system receives the data stream of digital image signals sent by the medical image acquisition device.

At step S704, the medical image processing system processes the received data stream of digital image signals in real time according to a predetermined image processing method so as to obtain optimized digital medical image signals.

In an embodiment of the present invention, said predetermined image processing method is an improved Gauss-Seidel iterative or Richardson-Lucy iterative algorithm. The particular descriptions regarding the improved Gauss-Seidel iterative or Richardson-Lucy iterative algorithm refer to those in corresponding sections of the image processing system of the present invention, and will not be described again.

In an embodiment of the present invention, the method further includes that the medical image processing system stores the optimized digital medical image signals locally or sends them to a remote storage center. In an alternative embodiment of the present invention, said processing method further includes that the medical image processing system provides the optimized digital medical image signals to a display apparatus for displaying images. In an alternative embodiment of the present invention, said processing method further includes that the medical image processing system receives patient information input by the display apparatus or imported from a database.

In an alternative embodiment of the present invention, the method further includes that the medical image processing system performs corresponding image processing on the optimized digital medical image signals according to the received image processing control instructions, which are received through control interfaces on the display apparatus and then sent to the medical image processing system, or received by a voice control module.

Although embodiments and advantages thereof have been described in detail, it should be understood that various changes, substitutions and modifications can be made to those embodiments without departing from the spirit of the present invention and scope thereof as set forth in the appended claims. With regard to other instances, those skilled in the art will appreciate that orders of processing steps can be changed within the scope of the present invention.

In addition, the present invention is not limit to be applicable to technology, construction, composition, means, method and step as described in this specification. From the disclosure of the present invention, as those skilled in the art will more readily appreciate that if functions or results achieved by the existing and future technology, construction, composition, means, method or step are largely similar with those of respective embodiments of the present invention, then they can be applied according to the present invention. Therefore, said technology, construction, composition, means, method or step is intended to be included within the scope of the appended claims.

The invention claimed is:

1. A medical image processing system including:
a signal transceiver that is configured to receive a data stream of digital image signals from a medical image acquisition device; and
an image processing module that is configured to process the received data stream of digital image signals in real time according to a predetermined image processing method so as to obtain optimized digital medical image signals that is remedied with respect to deficiency in definition,
wherein the image processing module is configured to perform the predetermined image processing method,
wherein the predetermined image processing method is an improved Gauss-Seidel iterative or Richardson-Lucy iterative algorithm, and
wherein said image processing module is configured to process the received data stream of digital image signals in real time according to the predetermined image processing method, which includes steps as follows:
S1: selecting an instrument characteristic matrix p(i,j);
S2: for each frame of matrix data d(i) of an input image, convolving d(i) with $p^T(i,j)$ as a re-convolution matrix c(i);
S3: proceeding to step S9 when the matrix data d(i) has no background or the background b(i) is known;
S4: calculating a normalized re-convolution matrix C*(i) of p(i,j) and d(i);

$$c^*(i) = \frac{M\Sigma_k[p(k,i)d(k)] - \Sigma_k p(k,i)\Sigma_k d(k)}{M\Sigma_k[p(k,i)]^2 - [\Sigma_k p(k,i)]^2};$$

where M are matrix data elements of each line of d(i);
S5: setting a threshold $f_m$, and determining whether each point of C*(i) is greater than $f_m$, if so, then determining whether this point is a data saltation point or has a value greater than that of the background,
calculating $d_b(k)=d(k)-p(k,i_s)f_s$, subtracting the value of this point;
where $f_s$ satisfies $\Sigma_i\{c_b(i')-[c^*(i)-f_s c_s(i,i_s)]\}^2=\min$,
and where $d_b(k)$ is a matrix data after subtracting the data saltation point and the data point having a value greater than that of the background, $d_b(i)$ is a re-convolution matrix of $d_b(k)$ and p(i,j), and $c_s(i; i_s)$ is a re-convolution matrix of p(i,j) and itself:

$$c_s(i; i_s) = \frac{M\Sigma_k[p(k,i)p(k,i_s)] - \Sigma_k p(k,i)\Sigma_k p(k,i_s)}{M\Sigma_k[p(k,i)]^2 - [\Sigma_k p(k,i)]^2}$$

repeating the above steps until all data points in C*(i) are less than $f_m$, so that matrix data, denoted as $d_b(k)$, in which the data saltation point and the data point having a value greater than that of the background are removed, is obtained;
S6: calculating the convolution of $d_b(k)$ and p(i,j), denoted as $c_b(i)$;
S7: restoring the background of data using the Gauss-Seidel iterative and Richardson-Lucy iterative algorithms, in which a set upper limit is that all values are greater than or equal to 0;
S8: repeating step S7 until a convergence result is obtained as a reconstructed background data, denoted as $b^{(1)}(i)$, where the superscript 1 indicates iterating one time;

S9: under a limitation of $b^{(l)}(i)$ or the background known in advance, calculating real matrix data, denoted as $f^{(l)}(i)$, by the Gauss-Seidel iterative or Richardson-Lucy iterative algorithm, where the superscript 1 indicates iterating one time and $f^{(1)}(i)$ represents the result after a first iteration;

S10: letting $f^{(l)}(i)$ satisfy a normalization condition:

$$\sum_k \sum_i p(k,i) f^{(l)}(i) = \sum_k d(k)$$

where $f^{(l)}(i)$ satisfying the normalization condition is the restored matrix data.

2. The medical image processing system according to claim 1, wherein at step S7, the background of data is restored with the Gauss-Seidel iterative algorithm by following formula:

$$b^{(l)}(i) = \frac{1}{p_1(i,i)} \left[ c_b(i) - \sum_{j \neq i} p_1(i,j) b^{(l-1)}(i) \right]$$

$$b^{(l)}(i) \geq 0$$

where $f^{(l)}(i)$ represents the result after the first iteration, and $p_1(i,i)$ is a result of multiplying $p(i,j)$ with $P^T(i,j)$.

3. The medical image processing system according to claim 1, wherein at step S7 the background of data is restored with the Gauss-Seidel iterative algorithm having a convergence factor by following formula:

$$b^{(l)}(i) =$$

$$\frac{\alpha}{p_1(i,i)} \left[ c_b(i) - \sum_{j=1}^{i-1} p_1(i,j) b^{(l)}(i) - \sum_{j=i+1}^{N} p_1(i,j) b^{(l-1)}(i) + (1-\alpha) b^{(l-1)}(i) \right]$$

$$b^{(l)}(i) \geq 0$$

where $\alpha$ is the convergence factor between 0 and 1.

4. The medical image processing system according to claim 1, wherein at step S7 the background of data is restored with the Richardson-Lucy iterative algorithm by following formula:

$$b^{(l)}(i) = b^{(l-1)}(i) \frac{\Sigma_j \frac{p(j,i) d(j)}{\Sigma_{i'} p(j,i') b^{(l-1)}(i')}}{\Sigma_j p(j,i)}$$

$$b^{(l)}(i) \geq 0.$$

5. The medical image processing system according to claim 1, wherein at step S9, the real matrix data is calculated with the Gauss-Seidel iterative algorithm by following formula:

$$f^{(l)}(i) = \frac{1}{p_1(i,i)} \left[ c(i) - \sum_{j \neq i} p_1(i,j) f^{(l-1)}(j) \right]$$

$$f^{(l)}(i) \geq b^{(l)}(i).$$

6. The medical image processing system according to claim 1, wherein in the step S9 the real matrix data is calculated with the Gauss-Seidel iterative algorithm having a convergence factor by following formula:

$$b^{(l)}(i) = \frac{\alpha}{p_1(i,i)}$$

$$\left[ c(i) - \sum_{j=1}^{i-1} p_1(i,j) f^{(l)}(j) - \sum_{j=i+1}^{N} p_1(i,j) f^{(l-1)}(j) + (1-\alpha) f^{(l-1)}(i) \right]$$

$$f^{(l)}(i) \geq b^{(1)}(i).$$

7. The medical image processing system according to claim 1, wherein at step S9 the real matrix data is calculated with the Richardson-Lucy iterative algorithm by following formula:

$$f^{(l)}(i) = f^{(l-1)}(i) \frac{\Sigma_j \frac{p(j,i) d(j)}{\Sigma_{i'} p(j,i') f^{(l-1)}(i')}}{\Sigma_j p(j,i)}$$

$$f^{(l)}(i) \geq b^{(l)}(i).$$

8. The medical image processing system according to claim 1, wherein said image processing module is a FPGA chip or a CPLD chip.

9. The medical image processing system according to claim 1, further including:
an information entry module that is configured to receive patient information input through a display apparatus or imported from a database.

10. A volatile computer readable storage medium, comprising a program, when executed, implementing following operations:
receiving a data stream of digital image signals sent by a medical image acquisition device;
processing the received data stream of digital image signals in real time in accordance with a predetermined image processing method so as to obtain optimized digital medical image signals that is remedied with respect to deficiency in definition wherein said image processing module processes the received data stream of digital image signals in real time according to the predetermined image processing method, which includes steps as follows in the sequence set forth:
S1: selecting an instrument characteristic matrix $p(i,j)$;
S2: for each frame of matrix data $d(i)$ of an input image, convolving $d(i)$ with $p^T(i,j)$ as a re-convolution matrix $c(i)$;
S3: proceeding to step S9 when the matrix data $d(i)$ has no background or the background $b(i)$ is known;
S4: calculating a normalized re-convolution matrix $c^*(i)$ of $p(i,j)$ and $d(i)$;

$$c^*(i) = \frac{M \sum_k [p(k,i) d(k)] - \sum_k p(k,i) \sum_k d(k)}{M \sum_k [p(k,i)]^2 - \left[\sum_k p(k,i)\right]^2};$$

where M are matrix data elements of each line of $d(i)$;
S5: setting a threshold $f_m$, and determining whether each point of $c^*(i)$ is greater than $f_m$, if so, then determining whether this point is a data saltation point or has a value greater than that of the background, calculating $d_b(k)=d(k)-p(k,i_s)f_s$, subtracting the value of this point;

where $f_s$ satisfies $\Sigma_i\{c_b(i')-[c^*(i)-f_s c_s(i',i_s)]\}^2=\min$, and where (k) is a matrix data after subtracting the data saltation point and the data point having a value greater than that of the background, $c_b(i)$ is a re-convolution matrix of $d_b(k)$ and $p(i,j)$, and $c_s(i;i_s)$ is a re-convolution matrix of $p(i,j)$ and itself:

$$c_s(i;i_s) = \frac{M\sum_k[p(k,i)p(k,i_s)] - \sum_k p(k,i)\sum_k p(k,i_s)}{M\sum_k[p(k,i)]^2 - [\sum_k p(k,i)]^2}$$

repeating the above steps until all data points in $c^*(i)$ are less than $f_m$, so that matrix data, denoted as $d_b(k)$, in which the data saltation point and the data point having a value greater than that of the background are removed, is obtained;

S6: calculating the convolution $d_b(k)$ and $p(i,j)$, denoted as $c_b(i)$;

S7: restoring the background of data using the Gauss-Seidel iterative and Richardson-Lucy iterative algorithms, in which a set upper limit is that all values are greater than or equal to 0;

S8: repeating step S7 until a convergence result is obtained as a reconstructed background data, denoted as $b^{(l)}(i)$, where the superscript 1 indicates iterating one time;

S9: under a limitation of $b^{(l)}(i)$ or the background known in advance, calculating real matrix data, denoted as $f^{(l)}(i)$, by the Gauss-Seidel iterative or Richardson-Lucy iterative algorithm, where the superscript 1 indicates iterating one time and $f^{(l)}(i)$ represents the result after a first iteration;

S10: letting $f^{(l)}(i)$ satisfy a normalization condition:

$$\sum_k\sum_i p(k,i)f^{(1)}(i) = \sum_k d(k)$$

where $f^{(l)}(i)$ satisfying the normalization condition is the restored matrix data.

* * * * *